US007414029B2

(12) United States Patent
Peri et al.

(10) Patent No.: US 7,414,029 B2
(45) Date of Patent: Aug. 19, 2008

(54) ANTAGONISTIC PEPTIDES OF PROSTAGLANDIN E2 RECEPTOR SUBTYPE EP4

(75) Inventors: Krishna G. Peri, St-Laurent (CA); Serge Moffett, St-Laurent (CA); Daniel Abran, Vaudreuil (CA); Annie Bergeron, Repentigny (CA)

(73) Assignee: Theratechnologies, Inc., Saint-Laurent, Quebec (CA)

( * ) Notice: Subject to any disclaimer, the term of this patent is extended or adjusted under 35 U.S.C. 154(b) by 303 days.

(21) Appl. No.: 10/968,872

(22) Filed: Oct. 19, 2004

(65) Prior Publication Data

US 2005/0164949 A1 Jul. 28, 2005

Related U.S. Application Data

(63) Continuation-in-part of application No. 10/444,516, filed on May 23, 2003, now abandoned.

(60) Provisional application No. 60/382,336, filed on May 23, 2002.

(51) Int. Cl.
*A61K 38/08* (2006.01)
*C07K 7/06* (2006.01)

(52) U.S. Cl. ........................... 514/15; 514/16; 530/328

(58) Field of Classification Search ....................... None
See application file for complete search history.

(56) References Cited

U.S. PATENT DOCUMENTS 5,605,814 A 2/1997 Abramovitz et al. ....... 435/69.1
5,759,789 A 6/1998 Abramovitz ............... 435/7.21

FOREIGN PATENT DOCUMENTS

WO WO 00/01445 1/2000
WO WO 00/16760 3/2000
WO WO 01/42281 6/2001

OTHER PUBLICATIONS

Ngo et al. "Computational Complexity, Protein Structure Prediction, and the Levinthal Paradox." The Protein Folding Problem and Tertiary structure Prediction. Ed. K. Merz and L. Le Grand. Birkhauser, Boston, Ma. 491-495.*

Berendsen, Herman. "A Glimpse of the Holy Grail?" Science, vol. 282, pp. 642-643. Oct. 23, 1998.*

Rudinger, J. (1976). Peptide Hormones (Ed. J.A. Parson). University Park Press. Baltimore pp. 1-7.*

MedlinePlus, A service of the U.S. national Library of Medicine and the National Institutes of Health. "Chornic renal failure." Feb. 20, 2008 [retrieved on Mar. 19, 2008] Retrieved from Internet: <http://www.nlm.nih.gov/medlineplus/ency/article/000471.htm>.*

The Foundation for IgA Nephropathy. "Chronic Renal Insufficiency" Feb. 7, 2008 [retrieved on Mar. 19, 2008], Retreived from the internet: <http://www.igan.ca/id76.html>.*

Bastien et al., "Cloning, functional expression , and characterization of the human prostaglandin E2 receptor EP2 subtype," *J. Biol. Chem.*, 269(16):11873-11877, 1994.

Bhattacharya et al., "Developmental changes in prostaglandin E2 receptor subtypes in porcine ductus arteriosus," *Circulation*, 100(16):1751-1756, 1999.

Bouayad et al., "Characterization of PGE2 receptors in fetal and newborn lamb ductus arteriosus," *Am. J. Physiol. Heart Circ. Physiol.*, 280(5):H2342-H2349, 2001.

Breyer et al., "Differentiation localization of prostaglandin E receptor subtypes in human kidney," *Am. J. Physiol.*, 270:F912-918, 1996.

Breyer et al., "Regulation of renal function by prostaglandin E receptors," *Kidney Int.*, 54 (Suppl. 67):S88-S94, 1998.

File WPIDS on STN. An. No. 2004-053231. New peptide antagonists of prostaglandin E2 receptor subtype EP4, useful for manufacturing a medicament for treating end-stage renal disease, acute renal failure, renal insufficiency or patent ductus arteriosus. Absrtact fir WO2003099857, EP1506220, CN162551, JP2006506327. Abstract only. 2004.

Freidlander et al., "PGE2 binding sites and PG-stimulated cyclic AMP accumulation in rat isolated glomeruli and glomerular cultured cells," *Mol. Cell. Endocrinol.*, 30:201-214, 1983.

Jacoby et al., "The cyclooxygenase-2 inhibitor celecoxib is a potent preventive and therapeutic agent in the min mouse model of adenomatous polyposis," *Cancer Res.*, 60(18):5040-5044, 2000.

Li et al., "Inhibition of prostaglandin synthesis in newborn pigs increases cerebral microvessel prostaglandin F2α and prostaglandin E2 receptors, their second messengers and vasoconstrictor response to adult levels," *J. Pharmacol. Exp. Ther.*, 278(1):370-377, 1996.

Lieberthal and Nigam, "Acute renal failure. II. Experimental models of acute renal failure: imperfect but indispensable," *Am. J. Physiol. Renal. Physiol.*, 278(1):F1-F12, 2000.

Morath et al., "Immunolocalization of the four prostaglandin E2 receptor proteins EP1, EP2, EP3, and EP4 in human kidney," *J. Am. Soc. Nephrol.*, 10:1851-1860, 1999.

Mutoh et al., "Involvement of prostaglandin E receptor subtype EP4 in colon carcinogenesis," *Cancer Res.*, 62(1):28-32, 2002.

Narumiya et al., "Prostanoid receptors: structures, properties, and functions," *Physiol. Rev.*, 79(4):1193-1226, 1999.

(Continued)

*Primary Examiner*—Anish Gupta
(74) *Attorney, Agent, or Firm*—Fulbright & Jaworski LLP

(57) ABSTRACT

Antagonistic peptides of prostaglandin E2 receptor subtype EP4 and their use in the treatment or prevention of medical conditions associated with oligouric nephropathy, bone resorption, abnormal intestinal crypt cell proliferation or patency of the ductus arteriosus and the like are provided herein. The antagonistic peptides of the present invention can include the following formula:

$$X\text{-}A\text{-}(R)_n Y_m$$

wherein "X" is a hydrogen atom or an amine protecting group producing a carbamate or an amide when reacting with the amine; "A" is L-(4,4')-biphenylalanine or D-(4,4')-biphenylalanine; "R" is an amino acid selected from the group consisting of threonine, serine, tyrosine, glutamic acid, alanine, leucine and glycine; "Y" is lysine; "n" is an integer ranging from 5 to 7; and "m" is an integer ranging from 0 to 2.

13 Claims, 10 Drawing Sheets

OTHER PUBLICATIONS

Nguyen et al., "The prostaglandin receptor EP4 triggers remodeling of the cardiovascular system at birth," *Nature*, 390:78-81, 1997.

Schlondorff et al., "Prostaglandins and other arachidonic acid metabolites in the kidney," *Kidney Int.*, 29:108-119, 1987.

Shattuck-Brandt et al., "Differential expression of matrilysin and cyclooxygenase-2 in intestinal and colorectal neoplasms," *Mol. Carcinog.*, 24(3):177-187, 1999.

Singer and Epstein, "Potential of dopamine A-1 angonists in the management of acute renal failure," *Am. J. Kidney Dis.*, 31(5):743-755, 1998.

Smith et al., "Effect of gestational age, corticosteroids, and birth on expression of prostanoid EP receptor genes in lamb and baboon ductus arteriosus," *J. Cardiovasc. Pharmacol.*, 37(6):697-704, 2001.

Sugimoto et al., "Distinct cellular localization of mRNAs for three subtypes of prostaglandin E receptor in kidney," *Am. J. Physiol.*, 266(5 Pt 2):F823-F828, 1994.

Tai et al., "Transcriptional induction of cyclooxygenase-2 in osteoblasts is involved in interkeukin-6-induced osteoclast formation," *Endocrinology*, 138(6):2372-2379, 1997.

Tornich et al., "Aqueous Solubilization of Transmembrane Peptide Sequences with Retention of Membrane Insertion and Function," *Biophysical J.*, 74:258-267, 1998.

Wright et al., "Prostanoid receptors: ontogeny and implications in vascular physiology," *Am. J. Physiol. Regul. Integr. Comp. Physiol.*, 281(5):R1343-1360, 2001.

* cited by examiner

```
                              SEQUENCE LISTING


<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 1

Thr Ser Tyr Glu Ala Leu
  1               5


<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 2

Thr Ser Tyr Glu Ala Leu Lys
  1               5


<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 3

Thr Ser Tyr Glu Gly Leu Lys
  1               5


<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 4

Thr Ser Tyr Glu Ala Leu Lys Lys
  1               5
```

-continued

```
<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 5

Thr Ser Tyr Glu Gly Leu Lys Lys
  1               5


<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 6

Thr Ser Tyr Glu Ser Leu Lys
  1               5


<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 7

Thr Ser Tyr Glu Ser Leu Lys Lys
  1               5


<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 8

Thr Ser Tyr Glu Ala Lys
  1               5


<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 9

Thr Ser Tyr Glu Ser Lys
  1               5


<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptides
```

-continued

```
<400> SEQUENCE: 10

Thr Ser Tyr Glu Ala Leu Lys Lys
  1               5


<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 11

Thr Ser Tyr Glu Ala Leu Lys Lys
  1               5


<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 12

Thr Ser Tyr Glu Ala Leu Lys Lys
  1               5


<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 13

Thr Ser Tyr Glu Ala Leu Gly Lys Lys
  1               5
```

ANTAGONISTIC PEPTIDES OF PROSTAGLANDIN E2 RECEPTOR SUBTYPE EP4

This application is a continuation-in-part application of prior application Ser. No. 10/444,516, filed May 23, 2003, which claims the benefit of provisional Application No. 60/382,336, filed May 23, 2002. The contents of these applications are incorporated into this specification by reference.

FIELD OF THE INVENTION

The present invention relates to antagonistic peptides of prostaglandin E2 receptor subtype EP4. More particularly, the present invention relates to peptidic antagonists of prostaglandin E2 receptor subtype EP4 and their use in the treatment of medical conditions associated with oligouric nephropathy, bone resorption, abnormal intestinal crypt cell proliferation or patency of ductus arteriosis.

BACKGROUND OF THE INVENTION

Prostaglandins are derived from the oxygenation of arachidonic acid by prostaglandin (PG) synthases. Prostaglandins mediate a wide variety of physiological actions, such as vasomotricity, sleep/wake cycle, intestinal secretion, lipolysis, glomerular filtration, mast cell degranulation, neurotransmission, platelet aggregation, leuteolysis, myometrial contraction and labor, inflammation and arthritis, patent ductus arteriosus, cell growth and differentiation. Prostanoids mediate their actions through binding to distinct receptors which belong to the super family of rhodopsin-like seven transmembrane helical receptors. These receptors are coupled to heterotrimeric G-proteins comprised of α, β and γ subunits which, upon activation, elicit alterations in cell calcium, initiate phosphoinositide hydrolysis, or promotion or repression of cyclic adenosine monophosphate synthesis (Narumiya, S. et al. 1999; *Physiol. Rev.* 79: 1193-1226.).

Of the five pharmacologically-distinct prostanoid receptors PGE2, PGI2, PGD2, PGF2α, and TxA2, four subtypes of PGE2 receptor are described (Ichikawa, et al. 1996). These are EP1, EP2, EP3, which have several splice variants, and EP4. Cloned human EP4 (also known as prostaglandin E2 receptor subtype EP4) is a 488 amino acid glycoprotein, linked to $G_{\alpha S}$, and is involved in the stimulation of adenylate cyclase and cAMP synthesis (U.S. Pat. Nos. 5,759,789 and 5,605,814). The EP4 receptor is expressed at high levels in the intestine, but at much lower levels in the lung, kidney, thymus, uterus and brain (Bastien, Y. et al. 1994; *J. Biol. Chem.* 269 (16): 11873-77). The EP4 receptor is involved in fluid filtration in the kidney, differentiation of monocyte/macrophage precursors into osteoclasts, proliferation of intestinal crypt cells, and patency of ductus arteriosus in the mammalian fetus.

PGE2 is abundantly produced in the kidneys and is involved in the regulation of renal microcirculation, salt and water transport, and renin release (Breyer, M. D. et al. 1998; *Kidney Int.* 54 (Suppl. 67): S88-94). All EP receptors are regionally distributed in the kidney structures (Morath, R. et al. 1999; *J. Am. Soc. Nephrol.* 10: 1851-60) and are associated with specific functions. All studies conducted on the distribution of EP receptors in the kidneys have shown that the EP4 receptor is uniquely expressed in glomeruli (Breyer, M. D. et al. 1996; *Am. J. Physiol.* 270: F912-918. Morath, R. et al. 1999; *J. Am. Soc. Nephrol.* 10: 1851-60). However, the presence of this receptor in other structures of the nephron, such as the collecting duct (Breyer, M. D. et al. 1998; *Kidney Int.* 54 (Suppl. 67): S88-94), the media of renal arteries and vasa recta (Morath, R. et al. 1999; *J. Am. Soc. Nephrol.* 10: 1851-60) has been separately reported. EP4 transcripts have also been found in juxtaglomerular granule cells, and is consistent with PGE2-induced cAMP synthesis in these cells. EP4 may therefore also play a role in renin secretion.

Glomerular prostaglandins are thought to affect filtration (Schlondoff, D. et al., 1987; *Kidney Int.* 29: 108-19) and renin release. PGE2 increases cAMP levels in isolated glomeruli (Freidlander, G. et al., 1983; *Mol. Cell. Endocrinol.* 30: 201-214). It was suggested that the EP4 receptor coupled to cAMP synthesis, may regulate glomerular filtration (Sugimoto, Y. et al. 1994; *Am. J. Physiol.* 266(5 Pt 2):F823-8). Using small molecule antagonists (Kohno, Y. et al. WO 00/16760) and peptide antagonists (Peri, K. G. et al. WO 00/01445), a direct role of the EP4 receptor in modulating kidney filtration and urine output has been demonstrated.

Bones undergo continuous remodeling, wherein bone formation is carried out by osteoblasts and bone resorption is carried out by osteoclasts. These processes are controlled by several humoral factors such as parathyroid hormone, estradiol, vitamin D, cytokines, growth factors and prostaglandins. It has been illustrated that osteoclast induction by interleukin-1 (IL-1) is inhibited by aspirin-like drugs (Tai, H. et al. 1997). PGE2 analogues with EP4 receptor agonistic activity (no specific agonists or antagonists to this receptor exist to date) promote osteoclast formation in co-cultures of mouse osteoblasts and bone marrow cells. Similar experiments using cells from EP4-knockout mice resulted in reduced osteoclast formation, suggesting a role of the EP4 receptor in osteoclastogenesis in mice (Narumiya et al. 1999).

The ductus arteriosus is a normal large, low resistance, shunt vessel in fetuses, facilitating the bypass of blood towards the lungs. Since the fetus does not use its lungs (oxygen is provided through the mother's placenta), fetal lungs are collapsed and pose a high resistance to blood flow. Hence, blood flows from the right ventricle through the ductus into the descending aorta. High levels of circulating prostaglandins, particularly PGE2, keep the ductus in the foots open. When the infant is born, the lungs are inflated, the pulmonary resistance drops, PGE2 levels decrease, the ductus begins to close, and blood from the pulmonary artery thus enters into the lungs. The high levels of oxygen in the new born often close the ductus, in most cases within 24 hours. Patent Ductus Arteriosus (PDA) is the condition wherein the ductus doesn't close. In cases of PDA, morbidity and mortality rates are directly related to the flow volume through the ductus arteriosus. A large PDA may cause pulmonary hypertension, edema, recurrent infections, and may lead to congestive heart failure, if left untreated over long periods. Development of pulmonary vascular obstructive disease may occur. It is estimated that if left untreated, the mortality rate is 20% by the age of 20, 42% by the age of 45, and 60% by the age of 60. Females are 2 to 3 times more likely than males to develop PDA.

PDA can be treated either by drugs such as Indomethacin, which is a prostaglandin synthesis blocker, or by corrective surgery. Indomethacin, however, has side effects on renal ischemia and renal hypofusion, resulting in ischemic renal failure in preterm infants. EP4 is expressed in fetal pig (Bhattacharya, M. et al. 1999; *Circulation* 100(16): 1751-6), fetal lamb (Bouayad, A. et al., 2001; *Am. J. Physiol. Heart Cir.c Physiol.* 280(5); H2342-9) and fetal baboon (Smith G. C. et al., 2001; *J. Cardiovasc. Pharmacol.* 37(6): 697-704) ductus arteriosus. Paradoxically, EP4 knock-out mice die after birth due to insufficient closure of ductus arteriosus (Nguyen, M. et al. 1997; *Nature,* 390: 78-81).

A selective peptidic antagonist of the EP4 receptor has been used in the treatment of fetal ductus arteriosus (Peri, K. G. et al., WO 00/01445 and Wright, D. H. et al. Am. J. Physiol. Regul. Integr. Comp. Physiol. 2001; 281 (5): R1343-60).

Prostaglandins, particularly PGE2, play an important role in intestinal crypt cell proliferation. In fact, the inducible prostaglandin synthesizing enzyme COX-2 was shown to be present in intestinal polyps, as well as in colon tumors (Shattuck-Brandt, R. L. et al., 1999*; Mol. Carcinog.* 24(3): 177-87). COX-2 selective blockers such as Nimesulide were used to prevent chemical induction of colon carcinogenesis (Jacoby, R. F. et al. 2000*; Cancer Res.* 60(18): 5040-4). Recently, the actions of PGE2 have been shown to be mediated by the EP4 receptor, as deduced from the low incidence of colon polyps in EP4−/− mice, due to azoxymethane and the efficacy of the EP4 selective antagonist ONO-AE2-227 in reducing aberrant crypt foci in azoxymethane-treated min mice (Mutoh, M. et al. 2002*; Cancer Res.* 62(1): 28-32).

There thus remains a need to develop selective peptide antagonists of the prostaglandin E2 receptor subtype EP4 and peptidomimetics thereof. More specifically, there remains a need to develop selective peptide antagonists of the prostaglandin E2 receptor subtype EP4 useful in the treatment and prevention of colon carcinogenesis, treating end-stage renal disease, acute renal failure and other conditions of renal insufficiency preventing bone resorption in osteoporosis, in addition to conditions preventing closing of the ductus (PDA) in the neonates.

The present invention seeks to meet these and other needs.

The present description refers to a number of documents, the content of which is herein incorporated by reference in their entirety.

SUMMARY OF THE INVENTION

Selective peptide antagonists of the prostaglandin E2 receptor subtype EP4 are described. These peptidic antagonists can be used for making pharmaceutical compositions in order to treat patients diagnosed with acute or progressive renal failure, osteoporosis, dental diseases and other diseases where bone loss is an integral part of the disease process, and patent ductus arteriosus or patients at risk of developing such diseases. More specifically, the present invention relates to a peptide antagonist of prostaglandin E2 receptor subtype EP4 having the following general formula:

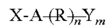

wherein "X" is a hydrogen atom or an amine protecting group producing a carbamate or an amide when reacting with the amine; "A" is L-(4,4')-biphenylalanine or D-(4,4')-biphenylalanine; "R" is an amino acid selected from the group consisting of threonine, serine, tyrosine, glutamic acid, alanine, leucine and glycine; "Y" is lysine; "n" is an integer ranging from 5 to 7; and "m" is an integer ranging from 0 to 2.

The present invention also relates to a composition comprising a peptide antagonist of prostaglandin E2 receptor subtype EP4 having the following general formula:

$$X\text{-}A\text{-}(R)_n\text{-}Y_m$$

wherein "X" is a hydrogen atom or an amine protecting group producing a carbamate or an amide when reacting with the amine; "A" is L-(4,4')-biphenylalanine or D-(4,4')-biphenylalanine; "R" is an amino acid selected from the group consisting of threonine, serine, tyrosine, glutamic acid, alanine, leucine and glycine; "Y" is lysine; "n" is an integer ranging from 5 to 7; and "m" is an integer ranging from 0 to 2.

In a preferred embodiment, the present invention relates to peptide antagonists of prostaglandin E2 receptor subtype EP4 selected from the group consisting of 213.15 (bip)tsyeal (SEQ ID NO: 1); 213.19 (bip)tsyealK (SEQ ID NO: 2); 213.20 (bip)tsyeglK (SEQ ID NO: 3); 213.21 (bip)tsyealKK (SEQ ID NO: 4); 213.22 (bip)tsyeglKK (SEQ ID NO: 5); 213.23 (bip)tsyeslK (SEQ ID NO: 6); 213.24 (bip)tsyeslKK (SEQ ID NO: 7); 213.25 (bip)tsyeaK (SEQ ID NO: 8); 213.26 (bip)tsyesK (SEQ ID NO: 9); 213.27 (Bip)tsyealKK (SEQ ID NO: 10); 213.28 (bip)tsyeaLKK (SEQ ID NO: 11); 213.29 (Bip)tsyeaLKK (SEQ ID NO: 12); and 213.30 (bip)tsyealGKK (SEQ ID NO: 13), wherein Bip is L-(4,4)-biphenylalanine and bip is D-(4,4)-biphenylalanine, and wherein D-amino acids are indicated in small letters and L-amino acids in capital letters. Amino acids are indicated in their single letter code.

The present invention also relates to selective peptidic or peptidomimetic forms of a prostaglandin E2 receptor subtype EP4 antagonist, capable of inhibiting at least one of the functional consequences of the receptor's activity.

The present invention also relates to pharmaceutical compositions comprising selective peptidic or peptidomimetic antagonists of prostaglandin E2 receptor subtype EP4, useful in treating end-stage renal disease, acute renal failure and other conditions of renal insufficiency preventing bone resorption in osteoporosis, as well as conditions preventing closing of the ductus (PDA) in the neonates.

The present invention also relates to pharmaceutical compositions comprising one or more peptide antagonists selected from the group consisting of labeled SEQ ID NOS: 1-13 and peptidomimetics thereof in association with one or more pharmaceutically acceptable carriers or excipients.

The present invention also relates to pharmaceutical compositions comprising one or more peptide antagonists selected from the group consisting of labeled SEQ ID NOS: 1-13 and peptidomimetics thereof, in association with one or more pharmaceutically acceptable carriers or excipients for increasing glomerular filtration and urine output.

The present invention also relates to pharmaceutical compositions comprising one or more peptide antagonists selected from the group consisting of labeled SEQ ID NOS: 1-13 and peptidomimetics thereof, in association with one or more pharmaceutically acceptable carriers or excipients for preventing bone loss experienced by patients suffering from osteoporosis, dental disease and cancer related conditions.

The present invention also relates to pharmaceutical compositions comprising one or more peptide antagonists selected from the group consisting of labeled SEQ ID NOS: 1-13 and peptidomimetics thereof, in association with one or more pharmaceutically acceptable carriers or excipients for effecting closure of the ductus arteriosus in medical conditions where patency of this blood vessel occurs.

The present invention also relates to pharmaceutical compositions comprising one or more peptide antagonists selected from the group consisting of labeled SEQ ID NOS: 1-13 and peptidomimetics thereof, in association with one or more pharmaceutically acceptable carriers or excipients for preventing or treating patients diagnosed with colon cancer or adenomatous polyps.

Furthermore, the present invention relates to the use of pharmaceutical compositions comprising one or more peptide antagonists selected from the group consisting of labeled SEQ ID NOS: 1-13, and peptidomimetics thereof for improving glomerular filtration and/or urine output of a patient diagnosed with end stage renal disease and acute renal failure.

Furthermore, the present invention relates the use of pharmaceutical compositions comprising one or more peptide antagonists selected from the group consisting of labeled SEQ ID NOS: 1-13, and peptidomimetics thereof for preventing bone loss experienced by patients suffering from osteoporosis, dental disease and cancer related conditions.

Furthermore, the present invention relates to the use of pharmaceutical compositions comprising one or more peptide antagonists selected from the group consisting of labeled SEQ ID NOS: 1-13, and peptidomimetics thereof for effecting closure of the ductus arteriosus in medical conditions where patency of this blood vessel occurs.

Furthermore, the present invention relates to the use of pharmaceutical compositions comprising one or more peptide antagonists selected from the group consisting of labeled SEQ ID NOS: 1-13, and peptidomimetics thereof for preventing or treating patients diagnosed with colon cancer or adenomatous polyps.

Moreover, the present invention relates to the use of one or more of the peptide antagonists selected from the group consisting of labeled SEQ ID NOS: 1-13 in a bioassay for identifying small molecule mimetics.

Finally, the present invention relates to a method of using the peptides or peptidomimetics of the present invention in an assay comprising the steps of: culturing cells or tissues expressing prostaglandin E2 receptor EP4 naturally or recombinantly; treating the cultured cells or tissues with a quantity of a peptide antagonist of prostaglandin E2 receptor subtype EP4 of the present invention or a peptidomimetic thereof in the presence or absence of a known concentration of an agonist of the receptor; and measuring one or more aspects of the bioactivity of the receptor, wherein the aspects are selected from the group consisting of GTP binding and hydrolysis by Ga proteins, cyclic adenosine monophosphate synthesis, alterations in cell calcium, cell growth and/or differentiation, altered gene expression and smooth muscle contraction or dilation.

It shall be understood that the peptide antagonists of the present invention and peptidomimetics thereof, can also be used for preventing medical conditions or diseases in which antagonists of prostaglandin E2 receptor subtype EP4 are warranted.

The use of the word "a" or "an" when used in conjunction with the term "comprising" in the claims and/or the specification may mean "one," but it is also consistent with the meaning of "one or more," "at least one," and "one or more than one." Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

It is contemplated that any embodiment discussed in this specification can be implemented with respect to any method or composition of the invention, and vice versa. Furthermore, compositions of the invention can be used to achieve methods of the invention.

The term "about" is used to indicate that a value includes an inherent variation of error for the device or the method being employed to determine the value.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

Having thus generally described the invention, reference will now be made to the accompanying drawings, showing by way of illustration a preferred embodiment thereof, and in which:

FIG. 1A shows the effects of 213.15 and corresponding derivatives (see Table 3) on the urine flow rate (expressed as μl of urine/h/kg body weight) in the rat model of ischemic nephropathy. FIG. 1B and FIG. 1C show the effects of 213.15 and corresponding derivatives (see Table 3) on the average glomerular filtration rate (GFR) over a period of 60 minutes (from 20 minutes to 80 minutes following injection of the drug, which was immediately after the removal of the clamps) in the rat model of ischemic nephropathy.

FIG. 2A shows the dose response of 213.29 on the GFR in normal beagle dogs. FIG. 2B shows the maximal effects of 213.29 on kidney function parameters in rat, dog and piglet.

FIG. 3 shows the effects of 213.29 on the dilation produced by PGE2 in porcine lower saphenous venous rings that are pre-contracted with U46619 (thromboxane A2 mimetic).

FIG. 4A shows the degradation profile of 213.29 in human serum. The peptide contains two lysines at the carboxy terminus which are susceptible to serum proteases. The degradation results in peptides lacking either one carboxyl lysine [213.291] or two carboxyl lysines [213.292]. The carboxyl leucine residue appears to be completely resistant to degradation by human serum under the experimental conditions. FIG. 4B shows the bioactivity of 213.29 and its metabolites in a cell based assay. Human EP4 expressing HEK293 cells were stimulated with 100 nM PGE2 in the presence or absence of 213.29 and its metabolites 213.291 and 213.292. cAMP levels determined by radioimmunoassay were expressed in pmol/$10^5$ cells.

FIG. 5 shows the effects of 213.29 on selective agonist-stimulated contractile responses of other prostanoid receptors (butaprost-EP2; 17-phenyl PGE2-EP1; PGF2a-FP; U46619-TP; M&B28767-EP3) in porcine retinal microvascular contractility assay.

FIG. 6A shows improvements in kidney function as assessed by glomerular filtration rate (GFR), renal plasma flow (RPF) and urine output in response to iv bolus (1 mg/kg) of 213.29 in the rat renal artery occlusion (RAO) model. As a control, fenoldopam (0.6 μg/kg bolus, followed by 0.6 μg/kg/h for the duration of the experiment) was used. FIG. 6B shows blood urea nitrogen (urea) and creatinine levels in response to 213.29 and fenoldopam in the rat RAO model (kidney function parameters are given in FIG. 6A), (Sham means sham-operated rats as control).

FIG. 7 shows a graphical representation of kidney histology (erythrocyte extravasation in periglomerular space and tubules presenting occlusions) in rats that underwent bilateral renal artery clamping for 1 hour and received qd (once daily) 1 mg/kg of 213.29 iv Bolus. The results show that 213.29 treatment significantly reduced periglomerular erythrocyte extravasation and tubular occlusion, leading to better recovery of kidney function in the rat model of ischemic acute renal failure.

FIG. 8 shows improvements in kidney function as assessed by RPF, GFR, and UV-urine flow rate, obtained with qd (once a day) and bid (twice a day) administration of 213.29 (1 mg/kg iv bolus) in animals that underwent bilateral renal artery clamping for 1 hour.

FIG. 9A shows kidney function parameters on day 5 in a rat model of acute tubular necrosis (rats injected with cisplatin ip 17.5 mg/kg on day 1). Glomerular filtration rate (GFR), renal plasma flow and urine output in saline (Sal)-treated rats, declined to extremely low levels by day 5; administration of 213.29 (1 mg/kg) on day 5 improved urinary parameters in saline-treated rats. However treating rats with 213.29 (5 mg/kg tid), starting on day 2, nearly normalized all parameters of kidney function by day 5; the improvement in kidney function correlated with decreases in blood urea nitrogen (BUN) and creatinine levels. FIG. 9B shows a graphical presentation of kidney histology from cisplatin-treated rats. 213.29 treatment (5 mg/kg tid) reduced hypertrophic glomeruli as well as the number of collecting ducts containing occlusions.

Figure 1A:
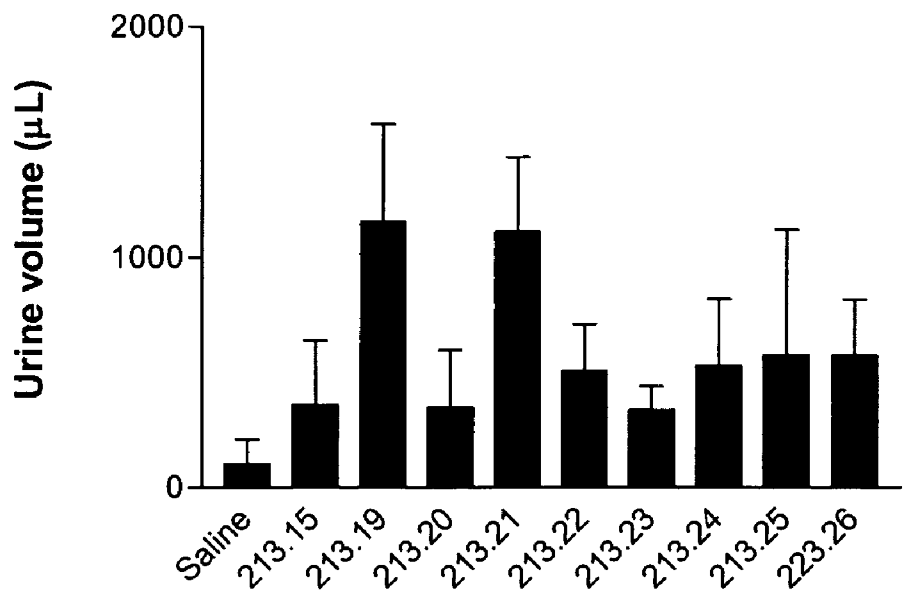
FIG. 1A, FIG. 1B and FIG. 1C.

EP4 mRNA, or molecules that bind to an EP4 polypeptide (e.g. peptides, peptidomimetics, antibodies, small molecules).

The term "amino acid", as used herein, is understood as including both the L and D isomers of the naturally occurring amino acids, as well as other non-proteinaceous amino acids used in peptide chemistry to prepare synthetic analogs of peptides. Examples of naturally-occurring amino acids include, but are not limited to glycine, alanine, valine, leucine, isoleucine, serine, and threonine. Examples of non-proteinaceous amino acids include, but are not limited to norleucine, norvaline, cyclohexyl alanine, biphenyl alanine, homophenyl alanine, naphthyl alanine, pyridyl alanine, and substituted phenyl alanines (substituted with a or more substituents including but not limited to alkoxy, halogen and nitro groups). Beta and gamma amino acids are also within the scope of the term "amino acid". These compounds are known to persons skilled in the art of peptide chemistry.

For the purpose of clarity, commonly accepted notations of amino acids are given below:

| FULL NAME | 3-LETTER CODE | 1-LETTER CODE | FULL NAME | 3-LETTER CODE | 1-LETTER CODE |
|---|---|---|---|---|---|
| Aspartic Acid | Asp | D | Threonine | Thr | T |
| Glutamic Acid | Glu | E | Glycine | Gly | G |
| Lysine | Lys | K | Alanine | Ala | A |
| Arginine | Arg | R | Valine | Val | V |
| Histidine | His | H | Leucine | Leu | L |
| Tyrosine | Tyr | Y | Isoleucine | Ile | I |
| Cysteine | Cys | C | Methionine | Met | M |
| Asparagine | Asn | N | Proline | Pro | P |
| Glutamine | Gln | Q | Phenylalanine | Phe | F |
| Serine | Ser | S | Tryptophan | Trp | W |

Other objects, advantages and features of the present invention will become more apparent upon reading of the following non-restrictive description of preferred embodiments with reference to the accompanying drawings, which is exemplary and should not be interpreted as limiting the scope of the present invention.

DESCRIPTION OF THE PREFERRED EMBODIMENTS

In order to provide a clear and consistent understanding of the terms used in the present specification, a number of definitions are provided below.

The term "agonist", as used herein, is understood as being an agent that potentiates at least one aspect of EP4 bioactivity. EP4 bioactivity can be increased for example, by stimulating the wild-type activity and by stimulating signal transduction, or by enabling the wild type EP4 protein to interact more efficiently with other proteins which are involved in signal transduction cascades.

The term "antagonist", as used herein, is understood as being an agent that inhibits or decreases at least one aspect of EP4 bioactivity. An EP4 antagonist can be a compound that inhibits or decreases the interaction between an EP4 molecule and another molecule, or decreases the synthesis and expression of an EP4 polypeptide, or inhibits the bioactivity of an EP4 molecule. The antagonist can be a nucleic acid molecule such as a dominant negative form of EP4, an EP4 antisense molecule, a ribozyme capable of specifically interacting with The term "polar amino acid", as used herein, is understood as referring to any amino acid containing an uncharged side chain that is relatively soluble in water.

The term "hydrophobic amino acid", as used herein, is understood as referring to any amino acid containing an uncharged side chain that is sparingly soluble in water.

The term "related amino acid", as used herein, is understood as referring to an alpha, beta or gamma substituted amino acid, natural or synthetic in origin, capable of mimicking the functionality of the side chain (e.g. aromatic, aliphatic, charged, polar, H-donor, H-acceptor). Examples of substitutions include, but are not limited to those provided in Tables 1 and 2.

The terms "biological activity", "bioactivity" or "biological function", as used interchangeably herein, are understood as referring to a function that is directly or indirectly performed by an EP4 polypeptide, or by any fragment thereof. Biological activities of EP4 include, but are not limited to binding to another molecule, interacting with other proteins, alterations in signal transduction such as guanine nucleotide binding by G$\alpha$ proteins, calcium fluxes, cAMP synthesis, inositol phosphate synthesis, internalization of EP4 polypeptide, associating with other intracellular proteins or coated pits in the cell membrane. A description of bioassays of the EP4 receptor is provided below.

The terms "cells", "host cells" or "recombinant host cells", as used interchangeably herein, are understood as referring not only to the particular cell, but to all its progeny. Also understood as being within the scope of these terms are cells of mammalian, amphibian, fungal, and bacterial origin.

The term "modulation", as used herein, is understood as referring to both upregulation [i.e., activation or stimulation (e.g., by agonizing or potentiating)] and downregulation [i.e. inhibition or suppression (e.g., by antagonizing, decreasing or inhibiting)].

The terms "protein" and "polypeptide", as used interchangeably herein, are understood as referring to a gene product.

The term "peptide", as used herein, is understood as referring to a linear polymer containing at least 2 amino acids and a maximum of about 50 amino acids. The amino acids can be naturally-occurring, or synthetically-derived molecules. Examples of such molecules include, but are not limited to L-amino acids, D-amino acids, and synthetic analogues of natural amino acids including but not limited to non-proteinaceous amino acids.

The term "peptidomimetic", as used herein, is understood as referring to a molecule that mimics the structural and/or functional features of a peptide. A person skilled in the art uses a variety of methods to derive peptidomimetics of a particular peptide such as, but not limited to: substitutions of individual amino acids with synthetic chemical entities, non-proteinaceous amino acid analogues, deletions and additions of amino acids, replacing one or more amino acids in the peptide with scaffolds such as beta turn mimetics, or with known pharmacophores. The objective of deriving a peptidomimetic is to obtain a superior molecular analogue of the peptide in terms of potency, efficacy, and which has a smaller size and has a better pharmacological and toxicological profile than the parent peptide.

The term "small molecule", as used herein, is understood as referring to a composition which has a molecular weight of less than about 1 kD and most preferably less than about 0.4 kD. Examples of small molecules include, but are not limited to nucleotides, amino acids, peptides, peptidomimetics, carbohydrates, lipids or other organic (carbon containing) molecules.

The term "another group of substitutions", as used herein, is understood as referring to exchanges within one of the five groups as depicted in Table 2.

The term "patient", as used herein, is understood as particularly referring to humans and includes any animal.

The present invention relates to a peptide antagonist of prostaglandin E2 receptor subtype EP4 having the following general formula as well as to compositions comprising such a peptide antagonist:

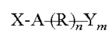

$$X\text{-}A\text{-}(R)_n\text{-}Y_m$$

wherein "X" is attached to the N-terminus of the peptide and is selected from the group consisting of a hydrogen atom, or an amine protecting group producing a carbamate or an amide when reacting with the amine. The amide comprises a hydrophobic moiety selected from the group consisting of cyclohexyl, phenyl, benzyl, linear $C_{1-8}$ alkyl and branched $C_{1-8}$ alkyl. Specific examples of amide groups are acetamide and benzamide.

"A" is L-(4,4')-biphenylalanine or D-(4,4')-biphenylalanine; "R" is an amino acid selected from the group consisting of threonine, serine, tyrosine, glutamic acid, alanine, leucine and glycine; "Y" is attached to the carboxy-terminus of the peptide and is a lysine residue; "n" is an integer ranging from 5 to 7; and "m" is an integer ranging from 0 to 2.

EP4 Antagonists

In the present invention a set of peptides have been synthesized, based on the sequence of peptide 213.15 (SEQ ID NO: 1). In order to improve on its solubility, a library of peptides containing various modifications of peptide 213.15 was synthesized, and characterized in terms of serum degradation, solubility, and pharmacological efficacy and potency in normal animals as well as in the rat model of acute renal failure. Based on these analyses, several peptides, more specifically peptides listed as Seq. ID Nos. 2-13, were identified.

Optimization of EP4 Antagonist 213.15 (SEQ ID NO: 1)

In order to improve the therapeutic efficacy of the peptidic lead compounds of the present invention, several modifications of the peptide were made by substituting one amino acid with a related amino acid or by adding amino acids to the carboxy terminus of the peptide. Substitutions of the amino acids of the EP4 peptidic antagonists of the present invention include, but are not limited to a variant wherein at least one amino acid residue in the polypeptide has been replaced by a different amino acid, either related by structure or by side chain functionality (aromatic, aliphatic and positively- or negatively-charged). Such substitutions are preferably made in accordance with the following description of relations among amino acids.

TABLE 1

Examples of related amino acids

| Residue | Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |
| Pro | Ala; Gly |

As illustrated in Table 2, another group of substitutions of the peptidic EP4 antagonists of the present invention involves those wherein at least one amino acid residue has been removed and is substituted by a different residue, which is inserted in its place.

TABLE 2

Relations among amino acids

| | |
|---|---|
| Small aliphatic, nonpolar or slightly polar residues | Ala, Ser, Thr (Pro, Gly) |
| Polar, negatively charged residues and their amides | Asp, Asn, Glu, Gln |
| Polar, positively charged residues | His, Arg, Lys |
| Large aliphatic, nonpolar residues | Met, Leu, Ile, Val (Cys) |
| Large aromatic residues | Phe, Tyr, Trp |

The three amino acid residues placed between parentheses in Table 2, play a special role in protein architecture. "Gly" is the only residue lacking any side chain and thus imparts flexibility to the chain. This however tends to promote the formation of a secondary structure other than the alpha-helical structure. "Pro", because of its geometry, tightly constrains the chain. It generally tends to promote beta turn-like structures. "Cys" is capable of participating in disulfide bond formation.

"Tyr", because of its hydrogen bonding potential, has significant kinship with "Ser" and "Thr".

Any amino acid component of the EP4 peptidic antagonists of the present invention can be substituted by its corresponding enantiomer (the same amino acid but of opposite chirality). Therefore, any amino acid naturally occurring in the L-configuration may be substituted by its corresponding enantiomer, that is, an amino acid having the D-configuration. Amino acids of the L-configuration have the same chemical structural type as the amino acids of the D-configuration, but have opposite chirality. The L- and D-configuration can also generally be referred to as R- or the S-configuration. Additional variations include β- and γ-amino acids, providing for a different spatial arrangement of chemical groups.

In addition to the substitutions outlined above, synthetic amino acids providing similar side chain functionality can also be introduced into the peptide. For example, aromatic amino acids may be replaced with D- or L-naphthylalanine, D- or L-phenylglycine, D- or L-2-thienylalanine, D- or L-1-, 2-, 3-, or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine D- or L-p-methoxybiphenylalanine, D- or L-2-indole(alkyl)alanines, and D- or L-alkylalanines wherein the alkyl group is selected from the group consisting of substituted or unsubstituted methyl, ethyl, propyl, hexyl, butyl, pentyl, isopropyl, iso-butyl, and iso-pentyl.

Non-carboxylate amino acids can be made to possess a negative charge, as provided by phosphono- or sulfated (e.g. —$SO_3H$) amino acids, which are to be considered as non-limiting examples.

Other substitutions may include unnatural alkylated amino acids, made by combining an alkyl group with any natural amino acid. Basic natural amino acids such as lysine and arginine may be substituted with alkyl groups at the amine ($NH_2$) functionality. Yet other substitutions include nitrile derivatives (e.g., containing a CN-moiety in place of the $CONH_2$ functionality) of asparagine or glutamine, and sulfoxide derivative of methionine. In addition, any amide linkage in the peptide may be replaced by a ketomethylene, hydroxyethyl, ethyl/reduced amide, thioamide or reversed amide moieties, (e.g. (—C═O)—$CH_2$—), (—CHOH)—$CH_2$—), ($CH_2$—$CH_2$—), (—C═S)—NH—), or (—NH—(—C═O) for (—C═O)—NH—)).

Covalent modifications of the peptides are thus included within the scope of the present invention. Such modifications may be introduced into EP4 peptidic antagonists by reacting targeted amino acid residues of the polypeptide with an organic derivatizing agent capable of reacting with selected side chains or terminal residues of the polypeptide. The following examples of chemical derivatives are provided by way of illustration only, and are not meant the limit the scope of the present invention. Cysteinyl residues may be reacted with alpha-haloacetates (and corresponding amines), such as 2-chloroacetic acid or chloroacetamide, to provide carboxymethyl or carboxyamidomethyl derivatives. Histidyl residues may be derivatized by reaction with compounds such as diethylpyrocarbonate (e.g., at pH 5.5-7.0) because this reagent is relatively specific for the histidyl side chain. p-Bromophenacyl bromide may also be used (e.g., where the reaction is preferably performed in 0.1M sodium cacodylate at pH 6.0). Lysinyl and amino terminal residues may be reacted with compounds such as succinic or other carboxylic acid anhydrides. Other suitable reagents for derivatizing alpha-amino-containing residues include compounds such as imidoesters (e.g. methyl picolinimidate); pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, such as phenylglyoxal, 2,3-butanedione, 1,2-cyclohexanedione, and ninhydrin, according to known method steps. The derivatization of arginine residues requires that the reaction be performed under alkaline conditions, because of the high pKa of the guanidine functional group. Furthermore, these reagents may also react with the amine groups of lysine, as well as with the arginine epsilon-amino group.

The specific modification of tyrosinyl residues per se is well-known. Specific and non-limiting examples include the introduction of spectral labels onto tyrosinyl residues by reaction with aromatic diazonium compounds or tetranitromethane. N-acetylimidazol and tetranitromethane may be used to form O-acetyl tyrosinyl species and 3-nitro derivatives, respectively.

Carboxyl side groups (aspartyl or glutamyl) may be selectively modified by reaction with carbodiimides (R'—N═C═N—R') such as 1-cyclohexyl-3-(2-morpholinyl-(4-ethyl)carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions. Glutaminyl and asparaginyl residues may be deamidated to the corresponding glutamyl and aspartyl residues.

Other modifications of the peptides of the present invention may include hydroxylation of proline and lysine; phosphorylation of the hydroxyl group of seryl or threonyl residues; methylation of the alpha-amino group of lysine, arginine, and histidine; acetylation of the N-terminal amine; methylation of main chain amide residues (or substitution with N-methyl amino acids) and, in some instances, amidation of the C-terminal carboxyl groups, according to methods known in the art.

Covalent attachment of fatty acids ($C_6$-$C_{18}$) to the peptides of the present invention confers additional biological properties such as for example protease resitance, plasma protein binding, increased plasma half-life, and intracellular penetration.

The above description of possible modifications of a lead peptide should not be considered as a limitation to the scope of the approaches, nor should it be considered as a limitation to the possible modifications that can be engineered using a lead peptide such as 213.15 as the template. Due to the complex nature of peptide folding, neither the receptor-bound conformation of the peptide antagonist, nor the effects of the modified peptides on EP4 bioactivity can be predicted with absolute certainty. Hence, those skilled in the art will readily appreciate that the modified peptides should be tested in bioassays as described in the present invention or in those known in the art to the person of ordinary skill, in order to confirm biological activity. Non-limiting examples of assays include receptor binding or modulation of ligand binding to the corresponding GPCR. Specific examples pertaining to GPCRs and more particularly to the EP4 receptor in terms of in vitro, ex vivo and in vivo assays are known to persons skilled in the art, and selected examples are depicted in the Figures and are described below.

EP4 Receptor Bioassays

There are many published methods of assaying EP4 bioactivity, using either purified or crude preparations of EP4 (cell-free assays; see below) from tissues or cells in which EP4 is recombinantly expressed in heterologous bacterial, fungal or mammalian expression systems.

Cell-free assays can be used to identify compounds which are capable of interacting with an EP4 protein, thereby modifying the activity of the EP4 protein. Such a compound can, for example, modify the structure of an EP4 protein and thereby affect its activity. Cell-free assays can also be used to identify compounds which modulate the interaction between an EP4 protein and an EP4 binding partner. An EP4 binding partner is PGE2. In a preferred embodiment, cell-free assays used for identifying such compounds consist essentially of a mixture containing a buffered solution, EP4 protein, EP4 binding partner and a test compound. A test compound can be for example, a peptide, a peptidomimetic, a small molecule, and a nucleic acid. For detection purposes, the binding partner can be labeled with a specific marker such as a radionuclide with a fluorescent compound or with an enzyme. The interaction of a test compound with an EP4 protein can then be detected by determining the level of the marker after an incubation step and a washing step. A statistically significant change (potentiation or inhibition) in the interaction of the EP4 and EP4 binding protein in the presence of the test compound, relative to the interaction in the absence of the test compound, indicates a potential agonistic effect (mimetic or potentiator) or antagonistic effect (inhibitor) of EP4 bioactivity for the test compound. Radiolabeled samples are counted and quantified by scintillation spectrophotometry. Binding ligands can be conjugated to enzymes such as acetyl choline esterase and bound EP4-binding partner can be quantified by enzyme assay.

Cell-free assays can also be used to identify compounds which interact with an EP4 protein and which modulate an activity of an EP4 protein. Accordingly, in one embodiment, an EP4 protein is contacted with a test compound, and the bioactivity of the EP4 protein is monitored. The bioactivity of the EP4 protein in cell-free assays include, but is not limited to GTP binding, GTP hydrolysis, dissociation of $G_\alpha$ proteins, adenylate cyclase activation, phospholipase (A2, beta, gamma and D isoforms) activation, phospholipid hydrolysis and cAMP synthesis. The methods of measuring these changes in the bioactivity of a GPCR protein are well known to those skilled in the art.

Cell-Based Assays of EP4 Bioactivity

EP4 bioactivity can also be measured using whole bacterial, fungal, amphibian or mammalian cells (see cell-based assays described below), in which the EP4 protein is recombinantly expressed as a native protein or as a fusion protein, (e.g. EP4 conjugated to antibody epitope tags, green fluorescent protein, $G\alpha$ or $\beta$-arrestin). Fusion proteins have certain advantages over native proteins; fusion proteins can provide direct detection of EP4 polypeptides or EP4 bioactivity in cells, tissues and organisms. Epitope (FLAG, HA, polyHIS, c-myc, etc.)-tagged EP4 can be useful in tracking the protein in cells and tissues by immunochemical staining methods, and may aid in the isolation of pure or substantially-pure proteins of EP4 through immunoaffinity chromatography. Green fluorescent protein (GFP) fusion to the EP4 protein can be used to locate and follow the movements of EP4, such as for example its aggregation or association with other cellular proteins, internalization, trafficking, degradation in endocytotic vesicles, in living or fixed cells. EP4 fusions of GFP and luciferase can be used to study and monitor dimer and oligomer formation and association with other signaling molecules. EP4-$G\alpha$ protein fusions can be used to measure GTP binding and hydrolysis by the G protein in response to agonists or antagonists, and these methods, known to persons skilled in the art, are used to screen and/or test small molecule compound libraries for agonist or antagonist activity. These examples illustrate, but are not intended to limit the potential fusion partners and their uses in basic and applied scientific studies.

Cell based assays can be used for example, to identify compounds that modulate the bioactivity of the EP4 protein, and the expression of an EP4 gene or those genes that are induced or suppressed in response to increased or decreased bioactivity of the EP4 protein. Accordingly, in one embodiment, a cell capable of producing EP4 is incubated with a test compound in the presence or absence of a natural or synthetic agonist/antagonist of EP4, and the bioactivity of EP4 is measured. The resultant alterations in the bioactivity of EP4 are compared to control EP4 producing cells, which have not been contacted with the test compound. These measurements are used to assess the potency, affinity and action of the test compound towards modulating EP4 bioactivity.

Methods of Treatment

The present invention provides for both prophylactic and therapeutic methods of treating a patient diagnosed with reduced urine output and acute or chronic renal impairment. Administration of a prophylactic agent can occur prior to the manifestation of symptoms characteristic of the EP4 aberrancy, such that the medical condition and its consequences are prevented or, alternatively, its progression delayed. In general, the prophylactic or therapeutic methods comprise administering a therapeutically effective amount of an EP4 antagonist to a subject in need thereof. As described in the present invention, examples of suitable EP4 antagonists and derivatives thereof include, but are not limited to peptides, peptidomimetics and small molecule mimetics.

Data supporting the therapeutic use of the EP4 antagonists of the present invention, and derivatives thereof, for the treatment of human renal insufficiency disorders characterized by reduced urine output, increased blood urea nitrogen (BUN) and creatinine levels, was obtained from animal models of nephropathy. Renal insufficiency in acute renal failure may arise due to ischemia, secondary to poor renal perfusion or due to nephrotoxic insults mediated by radiocontrast agents, antineoplastics, antibiotics, immunosuppressive agents and heavy metals. Two rat models in which renal insufficiency has been produced by bilateral renal artery occlusion (ischemic nephropathy) or cisplatin injection (acute tubular necrosis), have been well characterized and shown to approximate the renal damage suffered by human patients (see review by Lieberthal, W., Nigam, S. K. (2000); Am. J. Physiol. Renal. Physiol. 278(1): F1-F12). Both rat models were used to illustrate the utility of the EP4 antagonists of the present invention, and derivatives thereof, for improving renal damage as well as kidney function. Several examples are provided in which the use of the EP4 antagonists of the present invention, as well as derivatives thereof, showed improved glomerular filtration, renal blood flow and urine output in rats, dogs and pigs. It is expected that the pharmacological efficacy of the EP4 antagonists of the present invention, as illustrated in diverse species (rats, dogs and pigs) extends to human subjects as well, based on the similarities in receptor sequences and their tissue distribution.

Pharmaceutical Preparations of EP4 Antagonists

The toxicity and therapeutic efficacy of the EP4 antagonists of the present invention, such as the $LD_{50}$ (lethal dose to 50% of the population) and the $ED_{50}$ (the therapeutically effective dose in 50% of the population) can be determined by standard pharmaceutical procedures in experimental animals. The dose ratio between toxic and therapeutic effects is known as the therapeutic index, and which can be expressed as the $LD_{50}/ED_{50}$ ratio. Compounds that exhibit large therapeutic indexes are preferred. The dosage of such compounds lies preferably within a range of circulating concentrations that includes the $ED_{50}$ but with little or no toxicity. The dosage may vary within this range, depending on the dosage form employed and the route of administration. A dose may be formulated in animal models in order to obtain a circulating plasma concentration range that includes the $IC_{50}$ (the concentration of the test compound that achieves a 50% inhibition of the symptoms) as determined in in vitro and ex vivo assays and in animal studies. Such information can then be used to more accurately determine useful doses in humans. Plasma levels of EP4 antagonists can be measured, for example, by high performance liquid chromatography coupled with mass spectroscopy (HPLC-MS). The effective dose of an EP4 antagonist could be 0.01 micrograms to 100 mg/kg and is determined by the route of administration, pharmaceutical preparation and the mode of delivery.

Kits

Any of the compositions described herein may be comprised in a kit. In a non-limiting example, one or more of the peptide antagonists and/or peptidomimetics of the peptide antagonists can be provided in a kit, alone or in combination with additional reagents. The kits can comprise, in suitable container means, a peptide antagonist, a peptidomimetic of the peptide antagonist and/or a reagent. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the containers in close confinement for commercial sale. Such means may include injection or blow-molded plastic containers into which the desired vials are retained.

The present invention is illustrated in further detail by the following non-limiting examples.

EXAMPLE 1

Chemical Synthesis of Peptides

Several peptides, based on the structure of 213.15 (SEQ ID NO: 1), were synthesized using F-moc chemistry and the solid phase Merrifield peptide method. The structures of these peptides are listed in Table 3 (SEQ ID NOS: 2-13). The purity of the trifluoroacetate salts of these peptides was assessed by HPLC and mass spectroscopy. The general synthesis methods will be better understood by referring to the following treaties: "Solid phase peptide synthesis", Stewart & Young, W. H. Freeman Co. San Francisco, 1969; "The proteins", Erikson and Merrifield, Vol. 2. (ed. Neurath & Hill), Academic Press, New York 1976. The solubility of the peptides in water is also listed in Table 3.

TABLE 3

Synthesized peptide library, based on the structure of 213.15

| Seq ID No. | Peptide Number | Sequence (N to C)§ | Solubility (mg/ml)* |
|---|---|---|---|
| 1 | 213.15 | (bip)tsyeal | 0.2 |
| 2 | 213.19 | (bip)tsyealK | 2.8 |
| 3 | 213.20 | (bip)tsyeglK | 1.15 |
| 4 | 213.21 | (bip)tsyealKK | 24.5 |
| 5 | 213.22 | (bip)tsyeglKK | 24.5 |
| 6 | 213.23 | (bip)tsyeslK | 13.0 |
| 7 | 213.24 | (bip)tsyeslKK | 23.5 |
| 8 | 213.25 | (bip)tsyeaK | 6.0 |
| 9 | 213.26 | (bip)tsyesK | 8.0 |
| 10 | 213.27 | (Bip)tsyealKK | 23.0 |
| 11 | 213.28 | (bip)tsyeaLKK | 20.0 |
| 12 | 213.29 | (Bip)tsyeaLKK | 15.6 |
| 13 | 213.30 | (bip)tsyealGKK | 16.0 |

§Capital letters indicate L-amino acids; small letters indicate D-amino acids;
bip: D-(4,4) biphenyl alanine;
Bip: L-(4,4) biphenyl alanine.
*Solubility is determined in water.

EXAMPLE 2

Effect of 213.15 Derivatives on Glomerular Filtration and Urine Output in a Rat Model of Ischemic Nephropathy Bilateral clamping of the renal arteries for 30-60 minutes results in the reperfusion of the kidneys and associated sequelae such as a dramatic decrease in glomerular filtration rate, urine output and tubular cell death. This model reproduces some important consequences of oligouric renal failure in humans. The efficacy of various 213.15 derivatives in reversing the renal damage was measured.

Ischemic Nephropathy Model

Sprague-Dawley rats (250-300 g) were anesthetized and the jugular vein was canulated for infusion with the peptide or with saline. In addition, the carotid artery was canulated to measure the arterial blood pressure with a pressure transducer (Gould) and to collect blood samples. The urinary bladder was canulated to collect urine. After catheterization, an infusion (1.6 ml/hr) of a mixture of [$^3$H] inulin (8 μCi/hr), [$^{14}$C] aminohippuric acid (0.8 μCi/hr) and anesthetics (ketamine and xylazine; 9:1 w:w; 0.095 ml/ml) was started. The animals were allowed to stabilize for a further 40 minutes. Two urine samples were collected over 10 minute periods, (from 40 to 50 minutes, and from 50 to 60 minutes) to assess the stability of the basal GFR. Blood samples were collected at 45 and 55 minutes respectively. The left and right renal arteries were then clamped for a period of 60 minutes to induce an acute renal ischemia. After the ischemic period, the animals were treated with peptides, 213.19-213.30, (1 mg/kg iv bolus) or with saline via the jugular vein. Blood and urine samples were then collected every 20 minutes for an additional period of 2 hours. Glomerular filtration rates (GFR) and urine flow rates, (measured by the [$^3$H] inulin method) as well as renal plasma flow (measured by the [$^{14}$C] aminohippuric acid method), were determined at different times and averaged for a 60 minute (20-80 minutes following the drug administration) period.

Figure 1B:
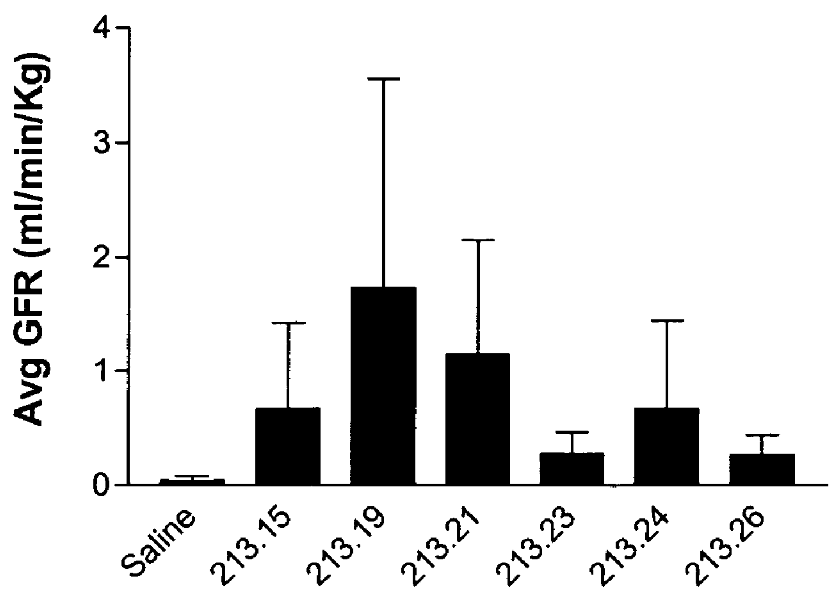

The results on the urine flow rate (FIG. 1A) and on GFR (FIG. 1B) are expressed as average urine flow rate and average GFR over a 60 minute period starting 20 minutes after the administration of the drugs. The order of efficacy for urine output was determined to be: 213.15>213.19≧213.21; other peptides were of similar efficacy to 213.15. Similarly, 213.19 and 213.21 also showed an increase in GFR. An improvement in GFR was not observed for the other peptides. Peptides 213.19 and 213.21 were consistently superior to the other peptides in causing improvements in GFR, urine flow rate and renal plasma flow.

Figure 1C:
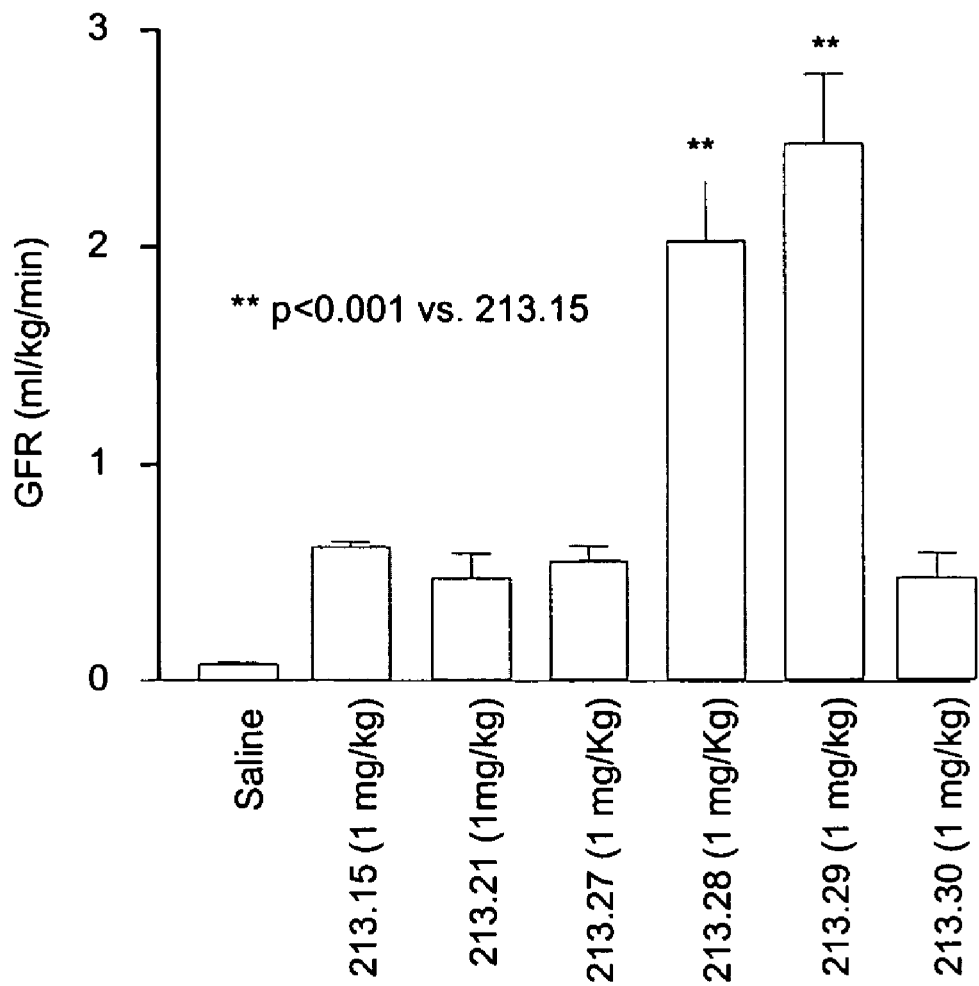

Based on the structure of 213.21, four more analogues, 213.27-213.30, were synthesized and tested in the rat model of renal artery occlusion. The results of GFR (averaged over 60 minutes and starting 20 minutes after the injection of the drug) are shown in FIG. 1C. For comparison, 213.15 and 213.21 are included in the figure. Both 213.28 and 213.29 increased GFR 4 and 5 fold, comparatively to 213.15, over the course of a 40 minute period following the unclamping of the renal artery. Of the compounds tested, 213.28 and 213.29, which are also more soluble (Table 3), are found to be more efficacious than the parent compound, 213.15.

EXAMPLE 3

Dose Response of 213.29 on Kidney Function in Normal Rat, Dog and Piglet

The dose response of 213.29 (1, 2, 3, 4, 5, 10 mg/kg bolus iv) was tested in anesthetized female Beagle dogs. Following an acclimation of at least one week, and overnight fasting, each animal was anesthetized with an iv injection of Thiopental (5 mg/Kg); the anesthesia was continued under isoflurane. The animal was kept warm and the body temperature monitored every 15 minutes. A carotid catheter for monitoring the blood pressure and a urethral catheter for collecting urine was installed. A constant iv infusion of saline (10 mL/kg/h), containing a total dose of 0.05 mCi of [$^3$H] inulin and 0.005 mCi of [$^{14}$C] para-aminohyppuric acid (PAH), sufficient for 5 hours of infusion, was initiated. A urine sample was collected every 10 minutes. In the middle of each 10-minute period, a blood sample was collected. After 60 minutes of equilibration of the radiolabels, incremental doses of 213.29 were injected intravenously via the cephalic vein.

Figure 2A:
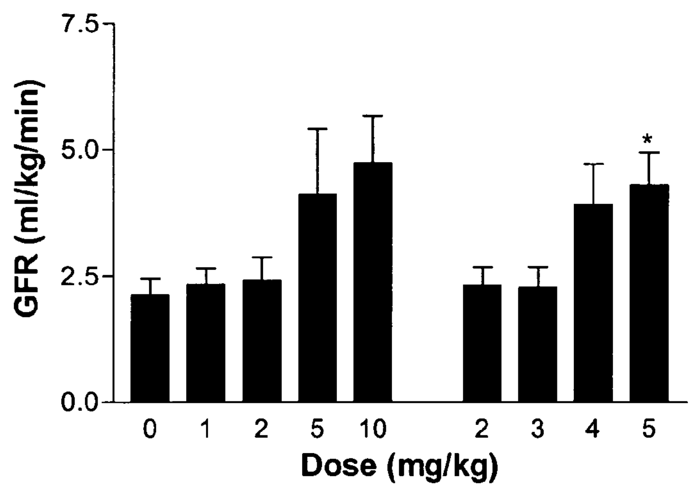
FIG. 2A and FIG. 2B.
Figure 2B:
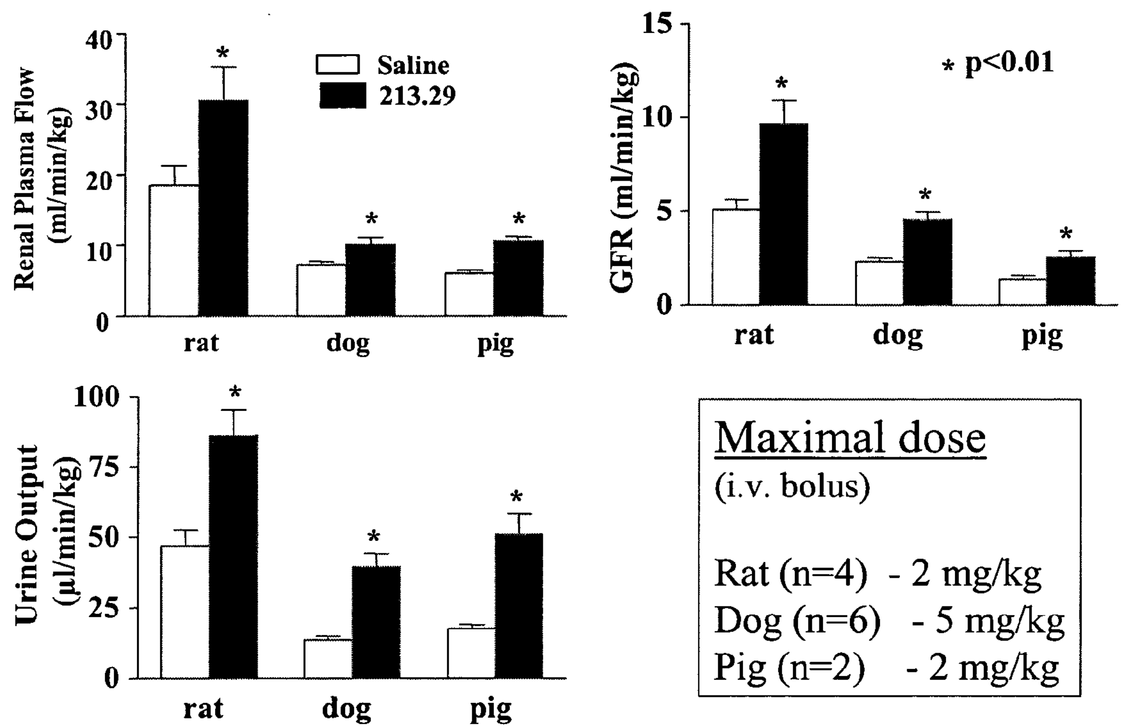

The radioactivity in the blood and urine samples (n=30/dog) was determined by scintillation spectrometry. The results of the study are shown in FIG. 2A. A dramatic and maximal increase in GFR as well as urine flow rate was observed at 4 mg/kg of 213.29 in normal dogs. FIG. 2B additionally shows the results of similar studies that were conducted in rats and piglets. The doses at which maximal responses in GFR, urine flow and renal plasma flow were observed, are indicated in the inset of FIG. 2B (n=number of animals). The results show that 213.29 causes increased renal perfusion, elevated GFR, and increased urine output in a species-independent manner. These results suggest that 213.29 would be effective in increasing renal perfusion, GFR and urine flow in humans.

EXAMPLE 4

Effect of 213.29 on PGE2-Induced Dilation of Porcine Lower Saphenous Venous Rings Animals Yorkshire piglets (2-4 days old) were used in this study, according to a protocol approved by the Animal Care Committee of the Research Center of the St.-Justine Hospital. Briefly, animals were anesthetized with halothane (1.5%) and the lower external saphenous veins removed and placed in cold Krebs buffer (pH 7.4) having the following composition (mM): NaCl 120, KCl 4.5, $CaCl_2$ 2.5, $MgSO_4$ 1.0, $NaHCO_3$ 27, $KH_2PO_4$ 1.0, glucose 10, to which 1.5 U/ml heparin was added.

Organ Bath Assay

The saphenous veins were cleaned of extraneous tissue and cut into 4 mm rings which were placed in individual jacketed organ baths (15 ml; Radnoti Glass, Monrovia, Calif.) containing Krebs buffer and maintained at 37° C. The solution was bubbled with an $O_2/CO_2$ mixture (95/5). In each experiment, 8 rings were used (4 from each saphenous vein) and were equilibrated for 60 minutes under 2.0 gr. passive tension with frequent washing and tension adjustment. The tension was measured by force-displacement transducers and was recorded on a computerized data acquisition system using the Work Bench software (both from Kent Scientific, Litchfield, Conn.).

Experimental Protocol

The vasodilatory response of the lower external saphenous veins to PGE2 appears to result from the stimulation of EP2 (30%) and EP4 (70%). The tissues were initially challenged with U46619 ($2\times10^{-7}$M) (thromboxane A2 mimic) which induced a 1.5 to 2.0 gr. increase in tension. The rings which did not respond were discarded. When the response to U46619 reached a steady state, agents were added. When no response to the agents were observed, a period of 30 minutes was allowed to insure proper distribution of the agents in the tissue. Dose-response curves to PGE2 ($10^{-10}$-$10^{-6}$M) were then obtained in the presence or absence of each of the tested drugs.

Figure 3:
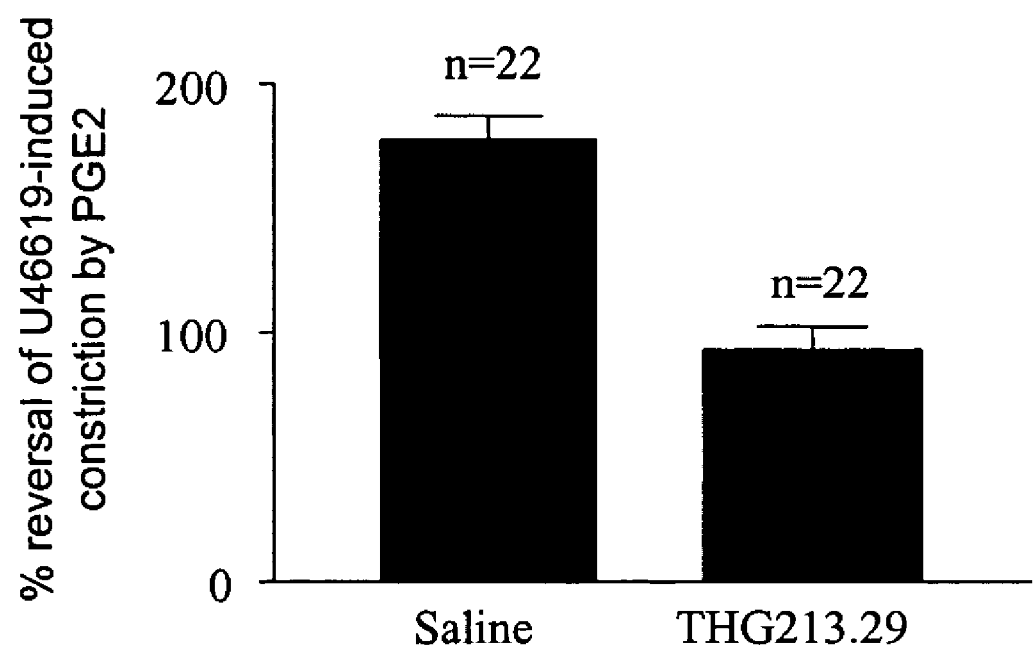
FIG. 3.

The results, which are an average of 2-8 experiments, are shown in FIG. 3. The results are expressed as percent reversal of dilation produced by 1 μM PGE2 in porcine lower saphenous venous rings pre-contacted with 1 μM U46619 (thromboxane A2 mimetic) in the presence of 1 μM of peptide. 213.29 reversed approximately 50% of the dilatory effect of PGE2 in this tissue.

EXAMPLE 5

Stability of 213.29 in Human Serum and the Biological Activity of the Metabolites The 213.29 peptide contains L-amino acids which could be susceptible to the action of serum proteases. In order to characterize the degradation products of 213.29, aliquots (100 μg) were incubated in human serum (0.5 ml) for varying periods of time at 37° C. The reaction was quenched with trifluoroacetic acid (0.24 ml; 1M), incubated on ice for 10 minutes following a further addition of TFA (0.25 ml; 0.05%), and centrifuged to precipitate the flocculates. The supernatants were purified by solid phase extraction on SepPak C18 cartridges. The peptide was eluted with 80% acetonitrile in 0.05% TFA and the eluates lyophilized. The peptide was then redissolved in acetic acid (400 μl of 0.1N) and subjected to separation by reverse phase HPLC on $C_{18}$ columns. The peak containing fractions were collected and the mass of the peptide fragments determined by MALDI-TOF.

Figure 4A:
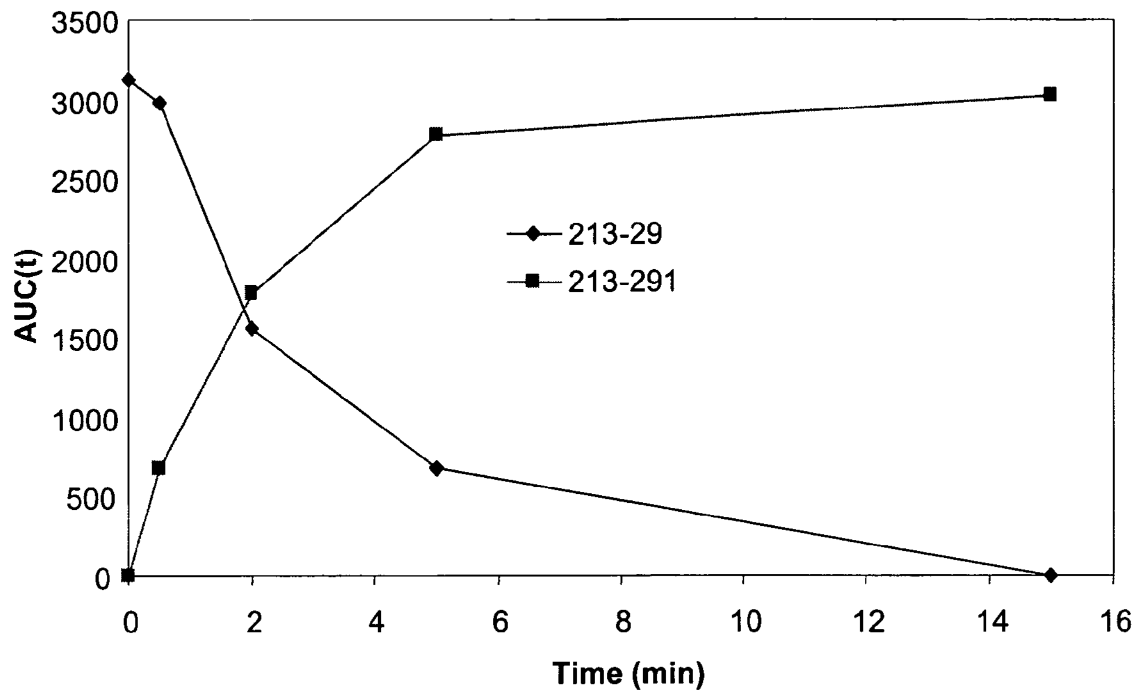
FIG. 4A and FIG. 4B.
Figure 4B:
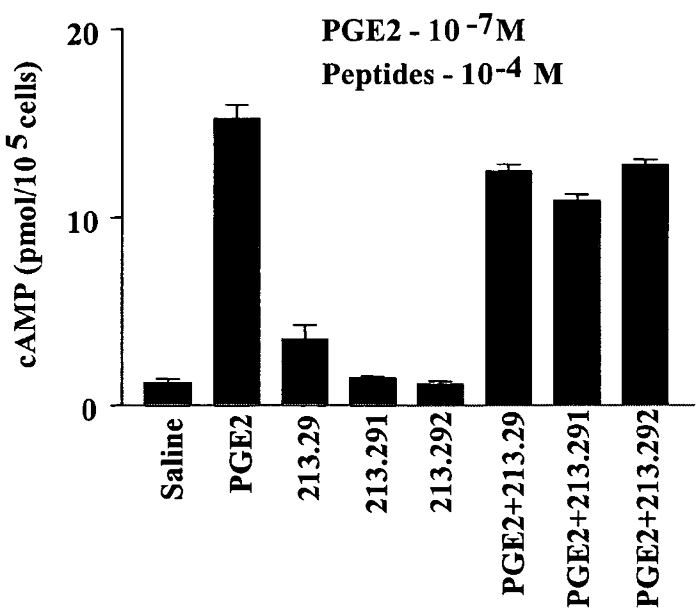

FIG. 4A shows the degradation of 213.29 over time, and the appearance of one of the metabolic products lacking one carboxyterminal lysine (213.291) (FIG. 4B). The cleavage was rapid with a half life of <2 minutes. The second metabolite, 213.292 (FIG. 4B) was not observed in the present experiment, and is slow to appear in the degradation reaction.

In order to test whether the metabolites also possessed biological activity, peptides 213.29, 213.291 and 213.292 were incubated with HEK293 cells recombinantly expressing human EP4 receptor, in the presence of 100 nM PGE2. cAMP levels were determined by radioimmunoassay and the results are illustrated in FIG. 4B. The peptides by themselves did not elicit stimulation of the receptor, but inhibited PGE2-stimulated cAMP synthesis by 20-30%.

EXAMPLE 6

Selectivity of 213.29 Antagonism to Prostanoid Receptor EP4

In order to demonstrate that 213.29 does not affect the biological responses of other prostanoid receptors, selective ligands (butaprost-EP2; 17-phenyl PGE2-EP1; PGF2a-FP; U46619-TP; M&B28767-EP3) of prostanoid receptors were used in an ex vivo assay of vascular constriction in porcine retinas which was previously described and validated (Li, D. Y., Abran, D., Peri, K. G., Varma, D. R., Chemtob, S. (1996); J. Pharmacol. Exp. Ther. 278(1): 370-7). Since prostanoid receptor densities in newborn vasculature are minimal, due to down regulation by high levels of circulating prostaglandins in the perinatal period, the newborn pigs were treated with a prostaglandin synthase blocker, ibuprofen (30 mg/Kg of bodyweight/8 h for 24 h) to increase the density of the receptors as well as their vasomotor effects.

Method

To prepare eyecups, a circular incision was made 3-4 mm posterior to the ora serrata, to remove the interior segment and vitreous body with minimal handling of the retina. The remaining eyecup was fixed with pins to a wax base in a 20 ml tissue bath containing 20 ml of Krebs's buffer (pH 7.35-7.45) and equilibrated with 21% oxygen and 5% carbon dioxide at 37° C. The preparations were allowed to stabilize for 30 minutes.

Figure 5:
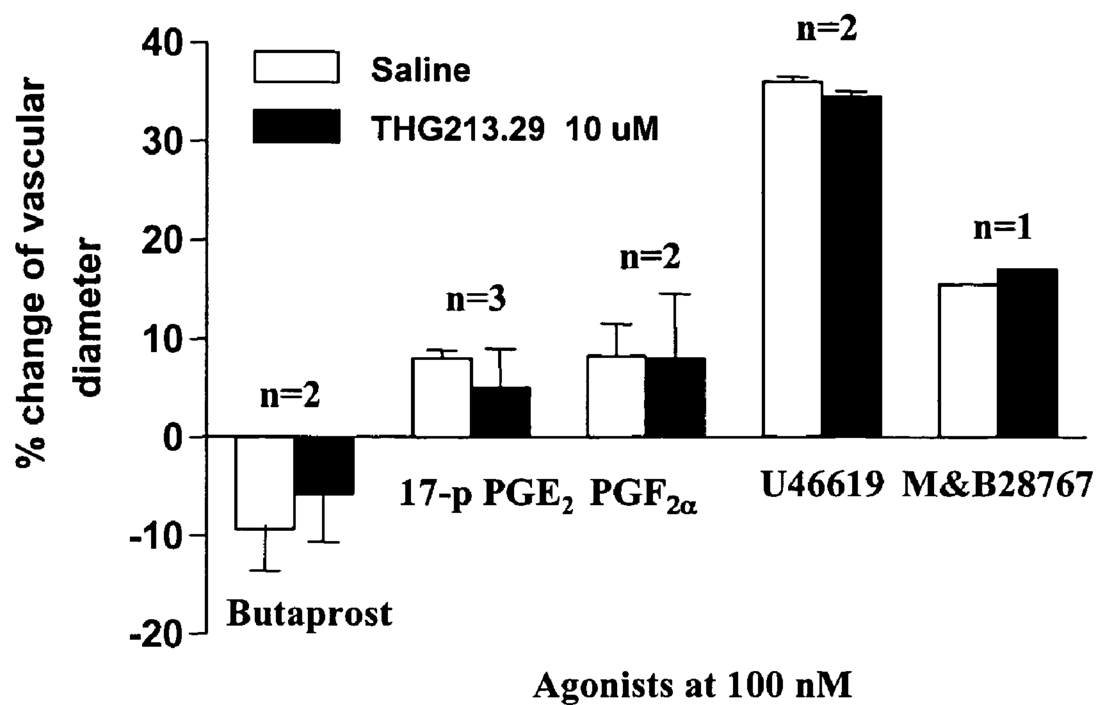
FIG. 5.

213.29 (10 μM) was added 5 minutes prior to the addition of 0.1 μM of ligands to the bath fluid. The outer vessel diameter was recorded with a video camera mounted on a dissecting microscope (Zeiss M 400) and the responses were quantified by a digital image analyzer (Sigma Scan Software, Jandel Scientific, Corte Madera, Calif.). The vascular diameter was recorded prior to, and 5 minutes following the topical application of the agonist. Each measurement was repeated three times and showed <1% variability. As shown in FIG. 5, 213.29 did not affect the contractile or dilatory responses of receptor selective agonists of prostanoid receptors. Thus 213.29 appeared to be highly selective to prostanoid receptor EP4.

EXAMPLE 7

Figure 6A:
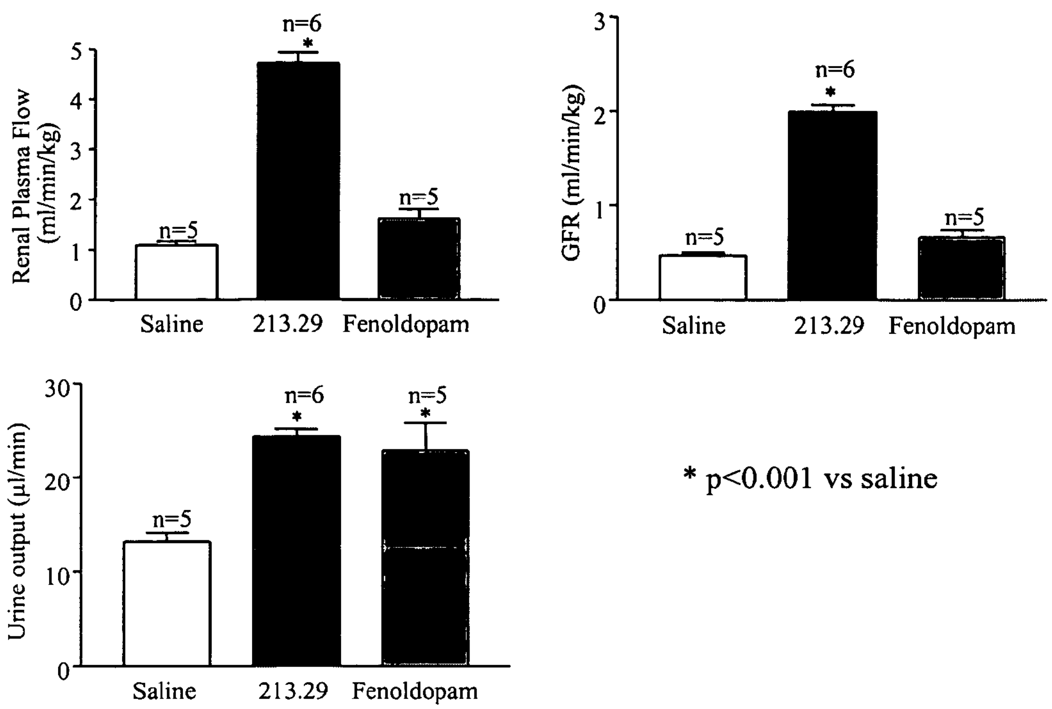
FIG. 6A and FIG. 6B.
Figure 6B:
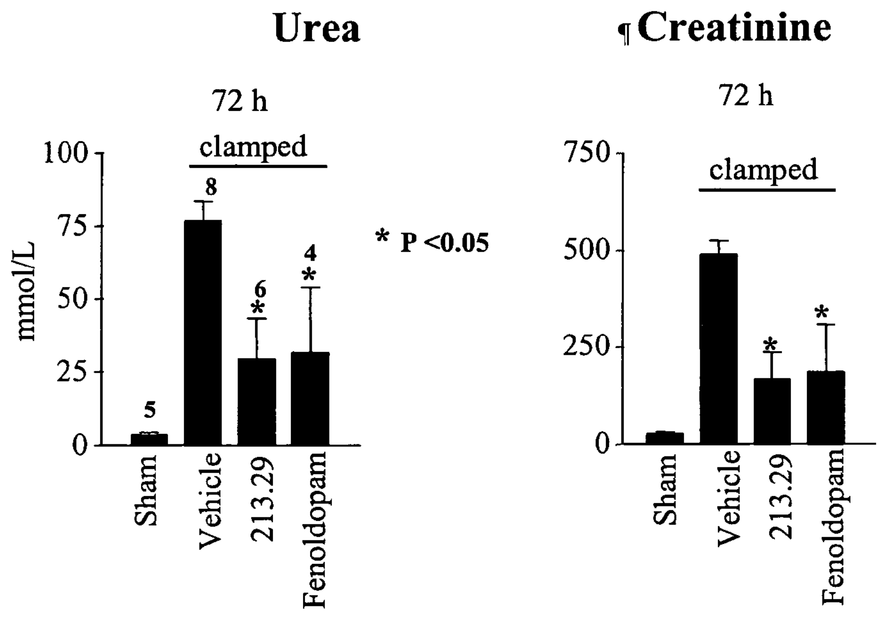

Comparison of 213.29 to Fenoldopam in the Improvement of Kidney Function in the Rat Model of Ischemic Nephropathy Fenoldopam is a dopamine receptor subtype 1 agonist, and has been shown to increase urine output in limited clinical and animal studies (Singer, I. and Epstein, M. 1998; Am. J. Kidney Dis. 31(5):743-55). The efficacy of fenoldopam and 213.29, in improving kidney function in the rat model of ischemic nephropathy (described in Example 2) was compared. 213.29 was given as an iv bolus of 1 mg/kg whereas fenoldopam was given as an iv bolus of 0.6 μg/kg followed by 0.6 μg/kg/h for the duration of the experiment. As shown in FIG. 6A, both fenoldopam and 213.29 increased urine output to a similar extent, but only 213.29 was able to improve renal perfusion and GFR significantly. Blood urea nitrogen (BUN) and serum creatinine levels were measured after 72 hours and as shown in FIG. 6B, both fenoldopam and 213.29 were equally efficacious in reducing BUN and creatinine levels.

EXAMPLE 8

Protective Effect of 213.29 Administration in Rats that Suffered Renal Failure (in the Rat Model of Ischemic Nephropathy)

The kidneys from the animals used in Example 7 were collected 24 hours or 72 hours after the unclamping of the renal arteries and drug dosing. An histological examination of sections was performed.

Figure 7:
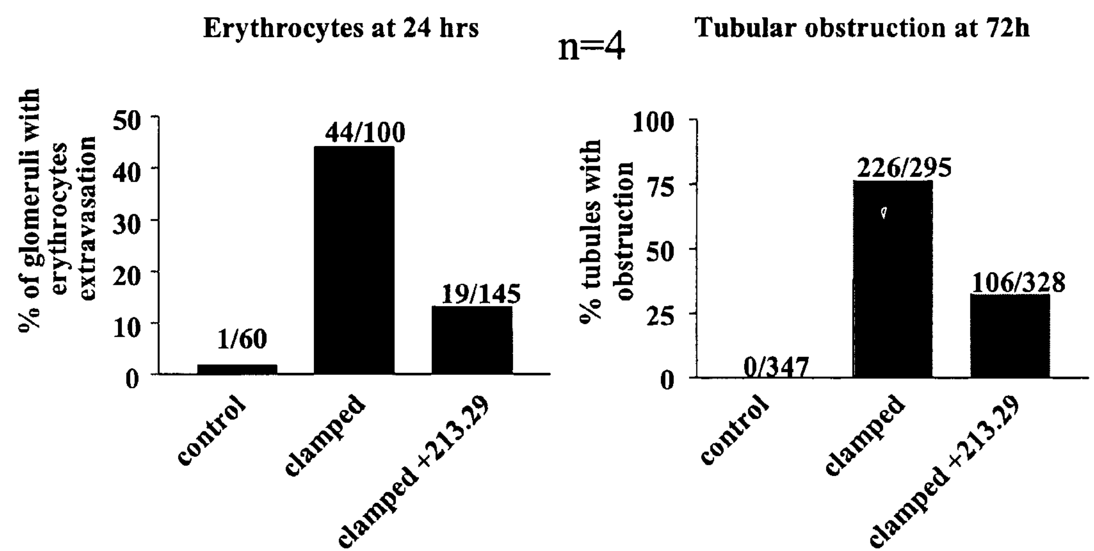
FIG. 7.

As shown in FIG. 7, the number of glomeruli showing periglomerular extravasation was significantly reduced as a result of the treatment with 213.29. Similarly, the number of collecting ducts containing cell debris was significantly reduced by 213.29. These results point to the use of 213.29 in improving kidney function as well as in protection from ultra structural damage, ensuing from ischemic insults.

EXAMPLE 9

Figure 8:
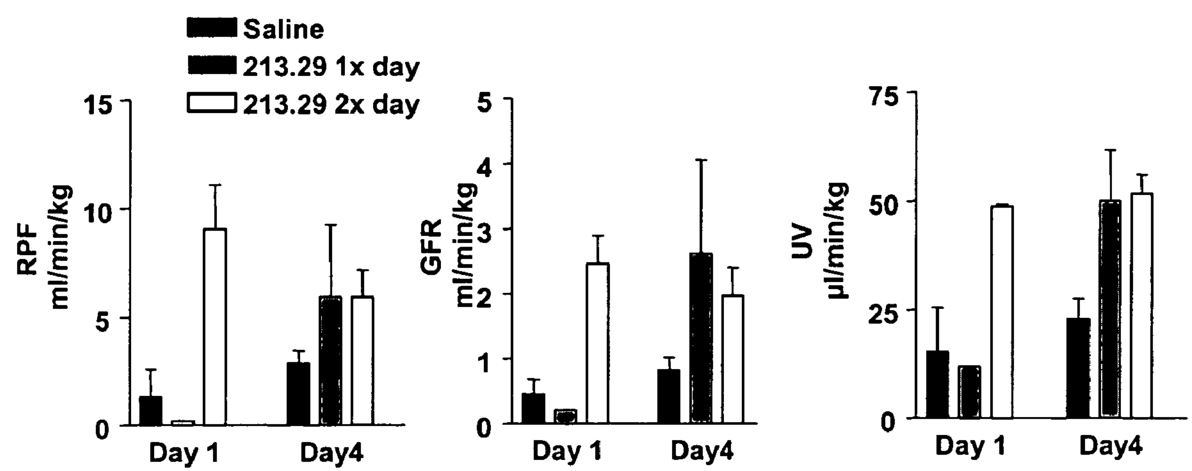
FIG. 8.

Effect of qd vs bid Administration of 213.29 in Rats that Suffered Renal Failure Due to Bilateral Renal Artery Clamping In order to determiner whether increasing the frequency of administration of 213.29 has a beneficial effect on kidney function in the rat RAO-model, 1 mg/kg of 213.29 iv was injected once (qd) or twice (bid) a day and the kidney function compared on day 1 and day 5. The results obtained are shown in FIG. 8. By day 4, the glomerular filtration rate (GFR), the renal plasma flow (RPF) and the urine flow rate (UV) improved to the same extent with a once a day (qd) or a twice a day (bid) administration. However, these parameters of kidney function showed a dramatic improvement on day 1 when the drug is administered twice a day rather than once a day. Thus frequent dosing of 213.29 in conjunction with the pharmacokinetics of the drug may improve the kidney function in cases of renal insufficiency.

EXAMPLE 10

Efficacy of 213.29 Administration in Rats that Suffered Acute Tubular Necrosis and Renal Failure Due to Cisplatin Acute tubular necrosis and renal failure are a direct consequence of the use of radiocontrast agents, neoplastic compounds and antibiotics. The rat cisplatin-induced acute tubular necrosis model was shown to reproduce many features of the human disorder [Lieberthal, W., Nigam, S. K. (2000); Am. J. Physiol. Renal. Physiol. 278(1):F1-F12].

Cisplatin-Induced Acute Tubular Necrosis Rat Model

Acute tubular necrosis was induced by injecting 17.5 mg/kg of cisplatin to Sprague-Dawley male rats on day 1. By day 5, the parameters of kidney function, namely GFR, RPF and UV, were dramatically reduced to negligible quantities (Sal [saline] column in FIG. 9A). This was followed by a 50% mortality in cisplatin-treated rats. Blood urea nitrogen (BUN) and creatinine levels increased dramatically by day 5 (data not shown).

Figure 9A:
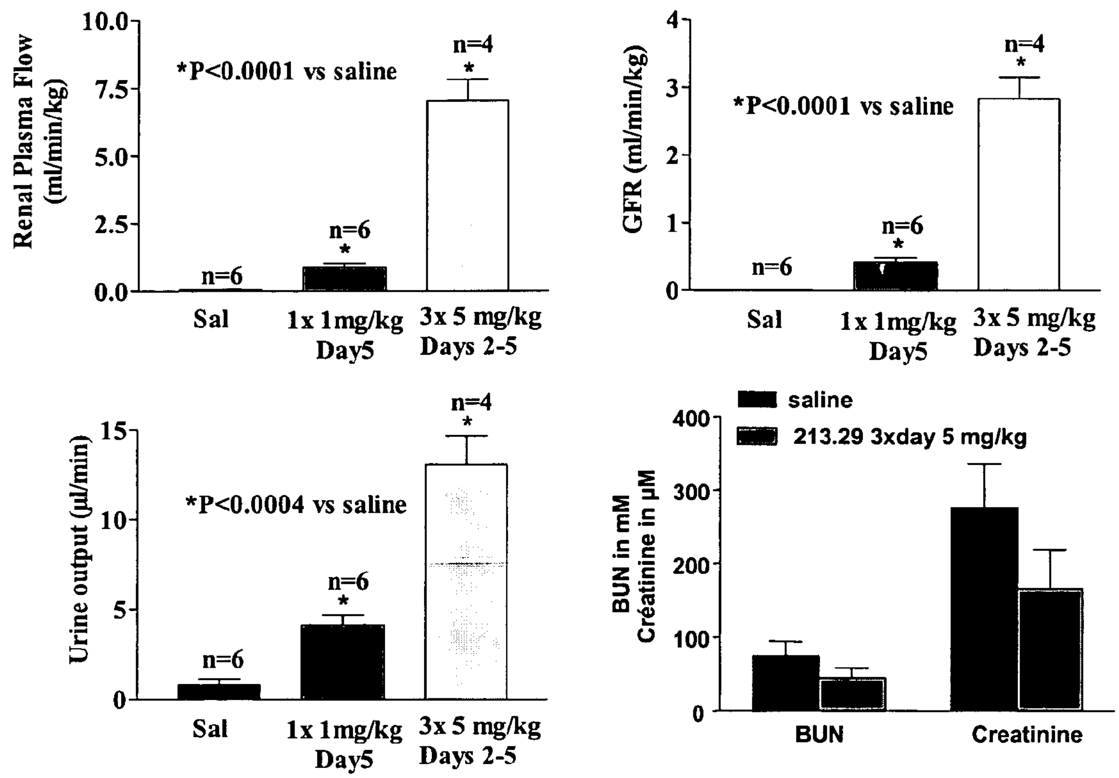
FIG. 9A and FIG. 9B.
Figure 9B:
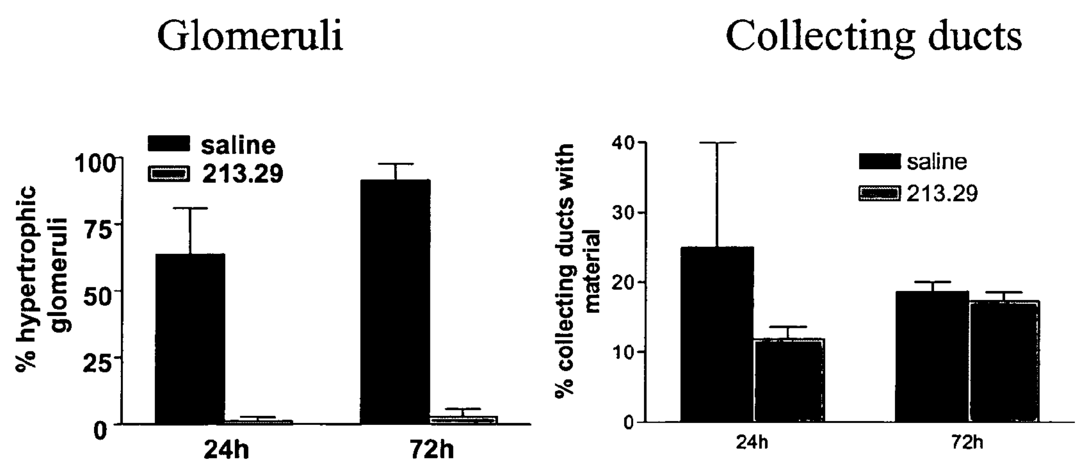

In order to determine whether 213.29 could still be useful in these conditions, kidney function tests were conducted after injecting the rats with 1 mg/kg iv on day 5. As shown in FIG. 9A, GFR, RPF and UV improved dramatically compared to the saline treated rats. The parameters of kidney function reached levels seen in normal healthy rats when the compound was given at 5 mg/kg three times a day (tid) starting on day 2 and continued till day 5 (FIG. 9A). Both blood urea nitrogen and creatinine levels were reduced as expected.

The obtained results in two rat models of renal insufficiency (very well validated and accepted in the literature [Lieberthal, W., Nigam, S. K. (2000); Am. J. Physiol. Renal. Physiol. 278(1):F1-F12] as models that reproduce important features of human acute renal failure due to ischemia or nephrotoxins), show that 213.29 and its derivatives improve kidney function and provide protection from exacerbation of renal damage. These compounds can therefore be used as therapeutic agents in human cases of acute renal failure and chronic renal insufficiency.

Although the present has been described hereinabove by way of preferred embodiments thereof, it can be modified, without departing from the spirit and nature of the subject invention as defined in the appended claims.

The invention claimed is:

1. A method for treating a human renal insufficiency disorder comprising administering a therapeutically effective amount of a peptide antagonist selected from the group consisting of: 213.19 D-(bip)-D-Thr-D-Ser-D-Tyr-D-Glu-D-Ala-D-Leu-Lys (SEQ ID NO: 2), 213.20 D-(bip)-D-Thr-D-Ser-D-Tyr-D-Glu-D-Gly-D-Leu-Lys (SEQ ID NO: 3), 213.21 D-(bip)-D-Thr-D-Ser-D-Tyr-D-Glu-D-Ala-D-Leu-Lys-Lys (SEQ ID NO:4), 213.22 D-(bip)-D-Thr-D-Ser-D-Tyr-D-Glu-D-Gly-D-Leu-Lys-Lys (SEQ ID NO:5), 213.23 D-(bip)-D-Thr-D-Ser-D-Tyr-D-Glu-D-Ser-D-Leu-Lys (SEQ ID NO:6), 213.24 D-(bip)-D-Thr-D-Ser-D-Tyr-D-Glu-D-Ser-D-Leu-Lys-Lys (SEQ ID NO: 7), 213.25 D-(bip)-D-Thr-D-Ser-D-Tyr-D-Glu-D-Ala-Lys (SEQ ID NO: 8), 213.26 D-(bip)-D-Thr-D-Ser-D-Tyr-D-Glu-D-Ser-Lys (SEQ ID NO: 9), 213.27 bip-D-Thr-D-Ser-D-Tyr-D-Glu-D-Ala-D-Leu-Lys-Lys (SEQ ID NO: 10), 213.28 D-(bip)-D-Thr-D-Ser-D-Tyr-D-Glu-D-Ala-Leu-Lys-Lys (SEQ ID NO: 11), 213.29 bip-D-Thr-D-Ser-D-Tyr-D-Glu-D-Ala-Leu-Lys-Lys (SEQ ID NO: 12) and 213.30 D-(bip)-D-Thr-D-Ser-D-Tyr-D-Glu-D-Ala-D-Leu-Gly-Lys-Lys (SEQ ID NO: 13), wherein bip is (4,4') biphenylalanine, to a patient in need thereof.

2. The method of claim 1, wherein the peptide antagonist is further comprised in a pharmaceutical composition.

3. The method of claim 1, further defined as administering from about 0.1 to about 100 mg of the peptide antagonist.

4. The method of claim 1, wherein the renal insufficiency disorder is acute renal failure, or chronic renal failure.

5. The method of claim 1, further defined as a method for improving glomerular filtration.

6. The method of claim 5, wherein improving glomerular filtration improves or increases urine output.

7. The method of claim 1, wherein the peptide antagonist is 213.29 bip-D-Thr-D-Ser-D-Tyr-D-Glu-D-Ala-Leu-Lys-Lys (SEQ ID NO: 12).

8. The method of claim 5, wherein the peptide antagonist is 213.29 bip-D-Thr-D-Ser-D-Tyr-D-Glu-D-Ala-Leu-Lys-Lys (SEQ ID NO: 12).

9. The method of claim 4, wherein the peptide antagonist is 213.29 bip-D-Thr-D-Ser-D-Tyr-D-Glu-D-Ala-Leu-Lys-Lys (SEQ ID NO: 12).

10. The method of claim 4, wherein the renal insufficiency disorder is acute renal failure.

11. The method of claim 10, wherein the peptide antagonist is 213.29 bip-D-Thr-D-Ser-D-Tyr-D-Glu-D-Ala-Leu-Lys-Lys (SEQ ID NO: 12).

12. The method of claim 4, wherein the renal insufficiency disorder is chronic renal failure.

13. The method of claim 12, wherein the peptide antagonist is 213.29 bip-D-Thr-D-Ser-D-Tyr-D-Glu-D-Ala-Leu-Lys-Lys (SEQ ID NO: 12).

* * * * *